United States Patent
Chatterjee et al.

(10) Patent No.: US 12,313,612 B2
(45) Date of Patent: May 27, 2025

(54) POLLUTION MONITORING SYSTEM AND METHOD THEREOF

(71) Applicant: INDIAN INSTITUTE OF TECHNOLOGY DELHI, New Delhi (IN)

(72) Inventors: Shouri Chatterjee, New Delhi (IN); Payali Das, New Delhi (IN); Sushmita Ghosh, New Delhi (IN); Swades De, New Delhi (IN)

(73) Assignee: INDIAN INSTITUTE OF TECHNOLOGY DELHI, New Delhi (IN)

( * ) Notice: Subject to any disclaimer, the term of this patent is extended or adjusted under 35 U.S.C. 154(b) by 413 days.

(21) Appl. No.: 17/954,019

(22) Filed: Sep. 27, 2022

(65) Prior Publication Data

US 2023/0101511 A1     Mar. 30, 2023

(30) Foreign Application Priority Data

Sep. 27, 2021 (IN) .............................. 202111043780

(51) Int. Cl.
*G01N 33/00*  (2006.01)
*B01D 46/42*  (2006.01)
(Continued)

(52) U.S. Cl.
CPC ..... *G01N 33/0073* (2013.01); *B01D 46/4245* (2013.01); *B01D 46/429* (2013.01);
(Continued)

(58) Field of Classification Search
CPC .......... G01N 33/0031; G01N 33/0063; G01N 33/0073; G01N 33/0075; G01N 1/2273;
(Continued)

(56) References Cited

U.S. PATENT DOCUMENTS

2002/0020208 A1\* 2/2002 Slater ...................... G01N 27/16
                                                    73/23.31
2016/0178585 A1\* 6/2016 Chien ................ G01N 33/0004
                                                    73/31.02

FOREIGN PATENT DOCUMENTS

CN         102665249 B        5/2015
CN         107462503 A       12/2017
(Continued)

OTHER PUBLICATIONS

Machine Learning Capable, IoT Air Pollution Monitoring System with Upgradable Sensor Array—C.S. Elvitigala, and B.H. Sudantha—Published in 2017.

*Primary Examiner* — Benjamin R Schmitt
(74) *Attorney, Agent, or Firm* — Jacob M. Ward; Ward Law Office LLC

(57) ABSTRACT

A pollution monitoring system and a method is disclosed. The pollution monitoring system comprises an on-board sensor unit having a plurality of sensors, configured for monitoring air quality by measuring pollution data in the air and a power control unit connected with the on-board sensor unit for controlling the operation of the on-board sensor unit. The pollution monitoring system further comprises microcontroller configured for generating control signals to be transmitted to the power control unit for controlling operation of on-board sensor unit. The microcontroller is configured for receiving information from a base station regarding operation of the on-board sensor unit. Further, the pollution monitoring system comprises an air purification unit configured for receiving the pollution data from the microcontroller and enabling activation or deactivation of the air purification unit based on comparison of the pollution data with predefined threshold values.

14 Claims, 6 Drawing Sheets

(51) Int. Cl.
  *B01D 46/44*  (2006.01)
  *B01D 46/46*  (2006.01)
  *H02S 10/20*  (2014.01)
  *G01N 1/22*   (2006.01)
  *H02J 7/35*   (2006.01)

(52) U.S. Cl.
  CPC ......... *B01D 46/442* (2013.01); *B01D 46/448* (2013.01); *B01D 46/46* (2013.01); *G01N 33/0031* (2013.01); *G01N 33/0063* (2013.01); *G01N 33/0075* (2013.01); *H02S 10/20* (2014.12); *G01N 1/2273* (2013.01); *H02J 7/35* (2013.01)

(58) Field of Classification Search
  CPC .............. B01D 46/442; B01D 46/4245; B01D 46/429; B01D 46/448; B01D 46/46
  See application file for complete search history.

(56) References Cited

FOREIGN PATENT DOCUMENTS

| | | | | | |
|---|---|---|---|---|---|
| GB | 2553375 | A | * | 3/2018 | ......... G01N 33/0031 |
| JP | 2005301835 | A | * | 10/2005 | ............ G08C 15/00 |
| WO | 2019210719 | A1 | | 11/2019 | |

* cited by examiner

POLLUTION MONITORING SYSTEM AND METHOD THEREOF

CROSS-REFERENCE TO RELATED APPLICATIONS AND PRIORITY

The present application claims priority to Indian application no. 202111043780, filed on Sep. 27, 2021.

TECHNICAL FIELD

The present subject matter described herein, in general, relates to pollution monitoring. More particularly, the present subject matter relates to an air pollution monitoring system and method.

BACKGROUND

Rapid industrial development, urbanization, has increased population and use of vehicles has proportionally increased the pollution levels specially in urban areas. Increased air pollution level is adversely affecting the health of the human and animal. Harmful effects of pollution include mild allergic reactions such as irritation of the throat, eyes and nose as well as some serious problems like bronchitis, heart diseases, pneumonia, lung and aggravated asthma. Thus, there is a need for large scale, fine-granular, and near-real-time pollution sensing along with pollution localization to timely reduce the air pollution levels.

Numerous technologies have been reported to monitor the pollution level. The reported pollution monitoring systems use advanced Internet of Things (IoT) based techniques to detect humidity, temperature, formaldehyde, CO2 and PM2.5. Further, advanced pollution monitoring device includes handheld devices with different applications pollution monitoring devices designed with multiple communication interfaces which include LoRa, NBIoT, RS485 and Wi-fi. The major drawback of these system is use of resistive heating and low battery lifetime. The wearable pollution monitoring sensors developed may be used along with smartphones to monitor environment CO, $NO_2$, $O_3$, temperature humidity and barometric pressure are being sensed with mote via Bluetooth. However, these sensors are not energy efficient and have complex system architecture. The battery-operated pollution monitoring system integrated with Bluetooth technologies for communication with cloud server have low communication range and may not be very useful for monitoring pollution over a large-scale area. Further, the pollution server is interfaced with Google Maps to display real time pollution value and further the sensing system may upload the gathered sensor data to the server using mobile network. However, any field testing or validation is not disclosed that may validate the data acquired.

Further, majority of the existing technologies use wi-fi or Bluetooth as the communication interface, which are having low range and consumes high power during communication. This drawback makes the sensor node hard for massive outdoor deployment. For massive deployment of sensor nodes, energy consumption is the major challenge that none of the existing technologies have addressed. Since consumption of PM sensor is typically high due to the high-power consuming fan used in it for inletting air inside the chamber, the Battery powered systems cannot serve this goal efficiently.

SUMMARY

Before the present pollution monitoring system and method is described, it is to be understood that this application is not limited to a particular pollution monitoring system and method, as there may be multiple possible embodiment, which are not expressly illustrated in the present disclosure. It is also to be understood that the terminology used in the description is for the purpose of describing the particular implementations, versions, or embodiments only, and is not intended to limit the scope of the present application. This summary is provided to introduce aspects related to pollution monitoring system and method thereof. This summary is not intended to identify essential features of the claimed subject matter nor is it intended for use in determining or limiting the scope of the claimed subject matter.

In one implementation, a pollution monitoring system is disclosed. The system comprises an on-board sensor unit having a plurality of sensors, configured for monitoring air quality by measuring pollution data in the air and a power control unit connected with the on-board sensor unit for controlling the operation of the on-board sensor unit. The system further comprises a microcontroller configured for generating control signals to be transmitted to the power control unit for controlling the operation of the on-board sensor unit. The microcontroller is configured for receiving information from a base station, regarding operation of the on-board sensor unit at each measurement cycle of measuring the pollution data and the information comprises sampling interval of the on-board sensor unit and number of sensors to be activated from the plurality of sensors in a next measurement cycle. The activation of the number of sensors is identified at the base station based on the pollution data collected by the microcontroller at a previous measurement cycle. Further, an air purification unit configured for receiving the pollution data from the microcontroller and enabling activation or deactivation of the air purification unit based on comparison of the pollution data with predefined threshold values.

In one implementation, a method facilitating pollution monitoring is disclosed. The method comprising measuring, through an on-board sensor unit having a plurality of sensors, pollution data in the air and controlling, through a power control unit connected with the on-board sensor unit, operation of the on-board sensor unit. The method further comprises generating, through a microcontroller, control signals to be transmitted to the power control unit for controlling the operation of the on-board sensor unit and receiving, through the microcontroller, information from a base station, regarding operation of the on-board sensor unit at each measurement cycle of measuring the pollution data. The information comprises sampling interval of the on-board sensor unit and number of sensors to be activated from the plurality of sensors in a next measurement cycle and the activation of the number of sensors is identified at the base station based on the pollution data collected by the microcontroller at a previous measurement cycle and shared with the base station. The method further comprises receiving, by an air purification unit, the pollution data from the microcontroller and enabling, by the microcontroller, activation or deactivation of the air purification unit based on comparison of the pollution data with predefined threshold values.

BRIEF DESCRIPTION OF DRAWING

The foregoing detailed description of embodiments is better understood when read in conjunction with the appended drawings. For illustrating the present subject matter, an example of construction of the present subject matter is provided as figures; however, the present subject matter is not limited to the specific pollution monitoring system and method thereof.

DETAILED DESCRIPTION

Some embodiments of this disclosure, illustrating all its features, will now be discussed in detail. The words "comprising", "including", "containing", "consisting", and other forms thereof, are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. Although any system or method or equivalent to those described herein may be used in the practice, the exemplary pollution monitoring system and method thereof is now described. The disclosed pollution monitoring system and method are merely examples of the disclosure, which may be embodied in various forms.

Various modifications to the embodiment will be readily apparent to those skilled in the art and the generic principles herein may be applied to other embodiments. However, one of ordinary skill in the art will readily recognize that the present disclosure for pollution monitoring system and method is not intended to be limited to the embodiments illustrated but is to be accorded the widest scope consistent with the principles and features described herein.

As disclosed in the background large scale, fine-granular, and near-real-time pollution sensing, and pollution localization are some important requirements for urban and industrial deployments. There are numerous pollution monitoring/controlling devices reported. However, these existing technologies are not energy efficient and having complex system architecture.

The present disclosure is directed to overcome one or more limitations stated above or any other limitation associated with the conventional arts.

Figure 1:
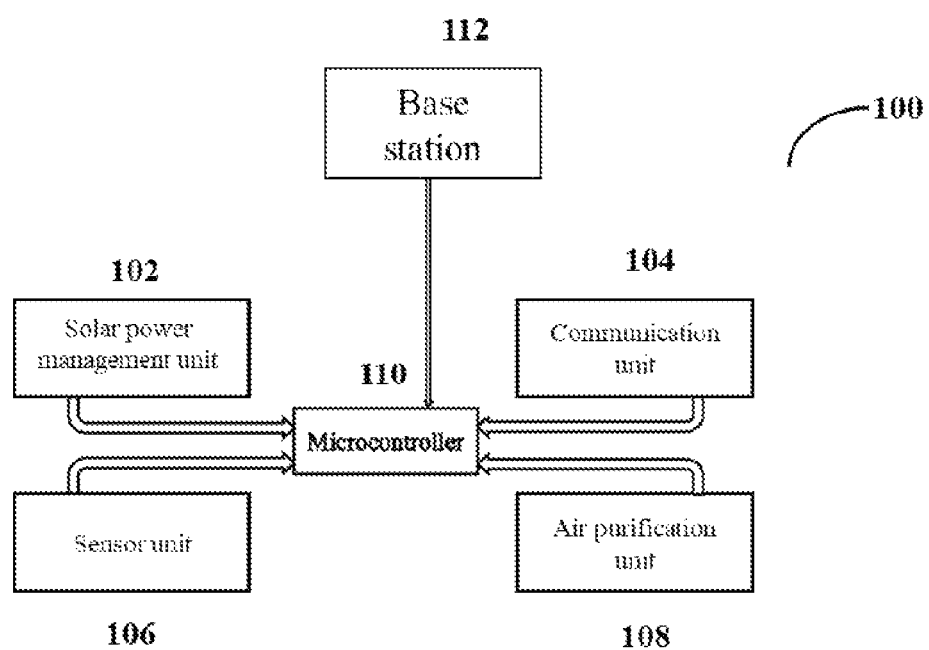
FIG. 1 illustrates a block diagram of pollution monitoring system, in accordance with an embodiment of the present subject matter.

In accordance with an embodiment, FIG. 1 illustrates an exemplary block diagram of a pollution monitoring system 100. The pollution monitoring system 100 will be described in detail by referring to FIG. 1 and FIG. 2 in combination. The pollution monitoring system 100 comprises an on-board sensor unit 106 having a plurality of sensors (106a-106d) (collectively referred as 106), configured for monitoring air quality by measuring pollution data in the air. The on-board sensor unit 106 comprise a temperature sensor 106d, a humidity sensor 106d, a gas sensor 106b, and a Particulate Matter (PM) sensor 106a.

In an embodiment, the pollution monitoring system 100 comprises a power control unit 102 connected with the on-board sensor 106 for controlling the operation of the on-board sensor unit 106. The power control unit 102 controls the operation of the on-board sensor unit 106 through a control signal generated by a microcontroller 110 and transmitted to the power control unit 102. The microcontroller 110 is configured to receiving information from a base station 112, regarding operation of the on-board sensor unit 106 at each measurement cycle of measuring the pollution data. The information received from the base station 112 comprises sampling interval of the on-board sensor unit 106 and number of sensors to be activated from the plurality of sensors (106a-106d) in a next measurement cycle. Further, the activation of the number of sensors (106a-106d) is identified at the base station 112 based on the pollution data collected by the microcontroller 110 at a previous measurement cycle.

In an embodiment control signal comprises a Pulse Width Modulation (PWM) signal applied at a switch to control activation period of the of fan used in the PM sensor 106c configured in the on-board sensor unit 106. The PWM signal is applied according to a duty cycle decided by the base station 112 and the duty cycle is decided according to availability of a rechargeable battery 102b powering the pollution monitoring system 100 along with signal reconstruction error threshold determined by the base station 112. In an embodiment, the PWM signal activates the fan at different duty cycles when the on-board sensor unit 106 measures the pollution data.

Further, the microcontroller 110 is configured to auto-calibrate the pollution data by using a polynomial regressor. One or more coefficients of the polynomial regressor are computed at the base station 112 and the coefficients are updated periodically at the on-board sensing unit 106 according to the control signal.

Figure 2:
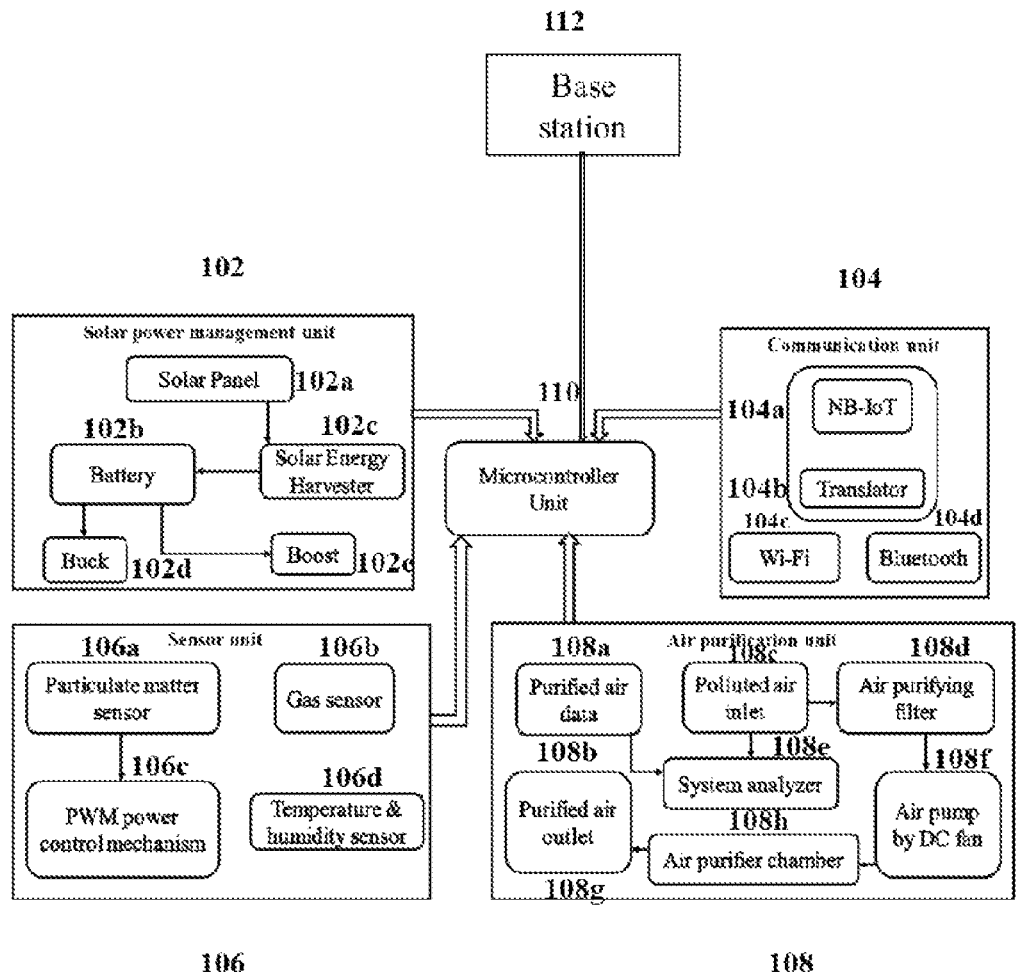
FIG. 2 illustrates additional details of the pollution monitoring system shown in FIG. 1, in accordance with an embodiment of the present subject matter.

Still referring to FIG. 1 and FIG. 2 in combination, the pollution monitoring system 100 comprises a power management unit 102 (also referred as a solar power management unit) configured to power the pollution monitoring system 100. The power management unit 102 comprise a solar panel 102a, the rechargeable battery 102b, and solar energy harvester 102c for harvesting energy from a solar cell (not shown in Figure) configured in the pollution monitoring system 100. The rechargeable battery 102b is configured for storing the energy harvested by the solar energy harvester 102c. The solar energy harvester 102c stores the energy in the rechargeable battery 102b. During daytime the required power is supplied from the solar cell. However, during night, the energy stored at the rechargeable battery 102b is used to continue the sensing and transmission operation of the pollution monitoring system 100.

In an embodiment, the pollution monitoring system 100 comprises an air purification unit 108 configured for receiving the pollution data from the microcontroller 110. The air purification unit 108 may be further configured to enable activation or deactivation of the air purification unit 108 based on comparison of the pollution data with predefined threshold values. The threshold value depends on the application of the pollution monitoring system 100 in a particular area. For example, the Air Quality Index (AQI) defining the threshold values for healthy living at one place may be considered as 60 while at some other place the AQI may be considered as 50.

In an embodiment, the air purification unit 108 comprises an air inlet 108c for receiving polluted air and a system analyzer 108e for comparing the pollution data associated with the polluted air with the predefined threshold values defined according to Air Quality Index (AQI). In case the pollution data exceeds the predefined threshold values, the purification system 108 is activated for producing purified air. Further, the purification unit 108 comprise an air purifying filter 108d for purifying the polluted air to be supplied to an air pump by a DC fan 108f and the polluted air is further supplied to an air purifier chamber 108h. The purification unit 108 further comprises a purified air outlet 108g for producing the purified air. Once the purified air is produced, the microcontroller 110 turns off the air purification unit 110 and thus saves the power.

In an embodiment, the pollution monitoring system 100 comprises a Global Positioning System (GPS) integrated with the communication unit 104 for tracking location of the pollution monitoring system 100. The microcontroller 110 transmits the location to the base station 112 and the location is transmitted at end of each ongoing measurement cycle. The GPS module further comprises a memory module configured for storing the pollution data at end of each monitoring cycle. The communication unit 104 may be further configure for establishing communication between the microcontroller 110 and the base station 112 and the communication unit 104 comprises a 5G eMTC protocol NB-IoT 104a, a Wi-Fi module 104c or a Bluetooth 104d.

In an embodiment, the base station 112 is configured for receiving pollution data from the microcontroller 110 at each measurement cycle. Further, the microcontroller 110 is connected to the on-board sensing unit 106 acting as the sensor node configured for measuring the pollution data. The base station 112 further determines the information regarding operation of the sensor node and the information is determined by using an adaptive sensing algorithm. The information comprises sampling interval of the on-board sensor unit 106 and number of sensors to be activated from the plurality of sensors (106a-106d) configured in the on-board sensing unit 106, in the next measurement cycle. The number of sensors activated is identified based on pollution data collected by the microcontroller 110 at the previous measurement cycle. In an embodiment the information is used by the microcontroller 110 for generating control signals controlling operation of each of the sensor node and an air purification unit 108 connected to the microcontroller 110 for purifying the air.

Figure 3:
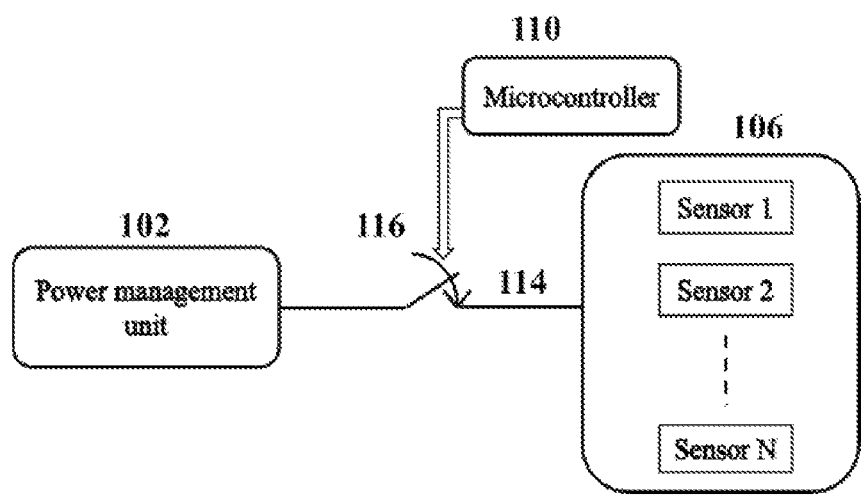
FIG. 3 illustrates Sensor power management system integrated with the pollution monitoring system, in accordance with an embodiment of the present subject matter.

In accordance with an embodiment, FIG. 3 shows the activation of the sensors (106a-106d) based on the sampling interval. The sensors are activated by applying the PWM signal at the switches connected to a power line 114 of the on-board sensing unit 106.

In an embodiment the base station 112 is further configured to enable, auto-calibration of the pollution data through the microcontroller 110 by generating coefficients of the polynomial regressor to be used by the microcontroller 110. Coefficients of the polynomial regressor determined by the base station 112 are updated periodically at the sensor node 106 according to the control signals.

Figure 4:
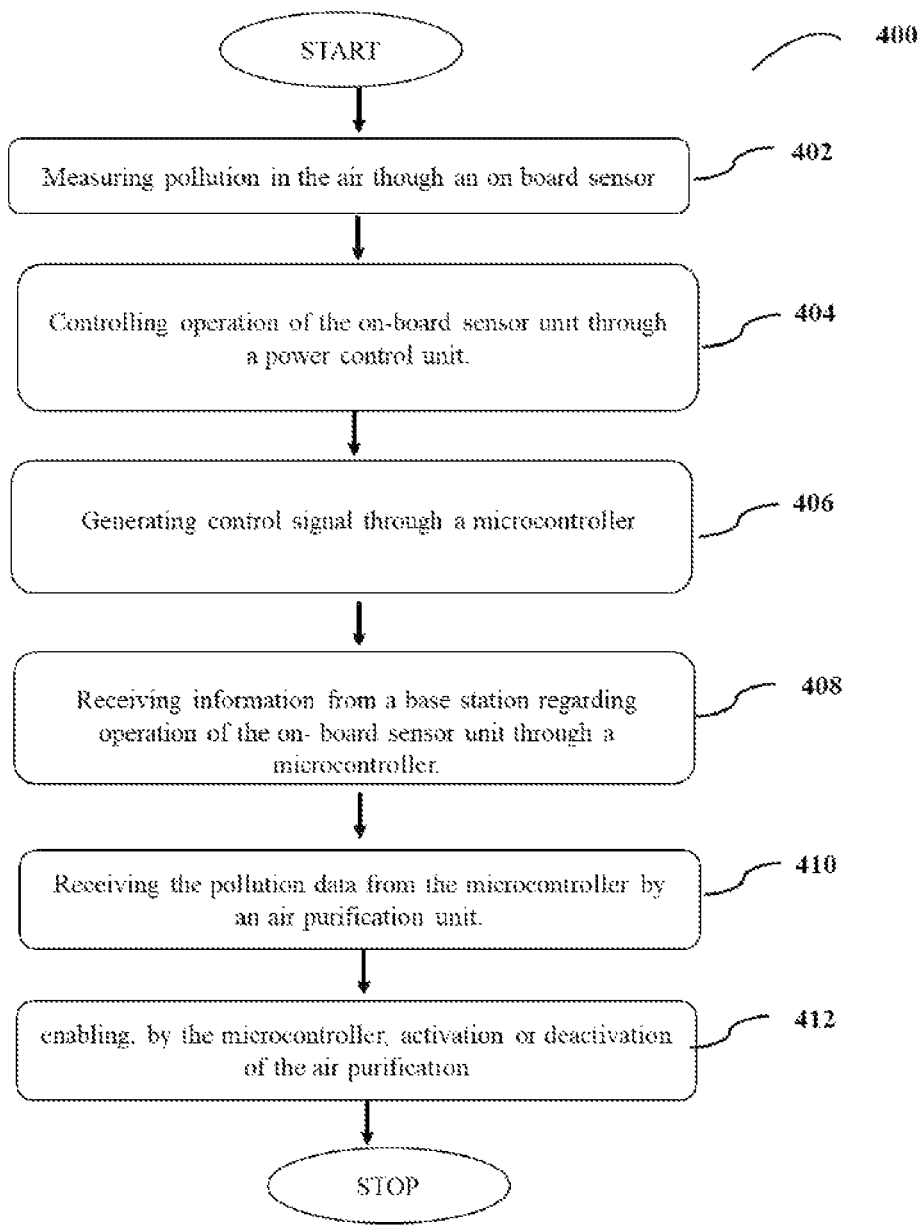
FIG. 4 illustrates a method facilitating pollution monitoring, in accordance with an embodiment of the present subject matter.

Referring to FIG. 4, a method 400 facilitating pollution monitoring, is disclosed in accordance with an embodiment of the present subject matter. The method 400 may be described in the general context of computer executable instructions. Generally, computer executable instructions can include routines, programs, objects, components, data structures, procedures, modules, functions, and the like, that perform particular functions or implement particular abstract data types. The method 400 may also be practiced in a distributed computing environment where functions are performed by remote processing devices that are linked through a communications network. In a distributed computing environment, computer executable instructions may be located in both local and remote computer storage media, including memory storage devices.

The order in which the method 400 is described is not intended to be construed as a limitation, and any number of the described method blocks can be combined in any order to implement the method 400 or alternate methods. Additionally, individual blocks may be deleted from the method 400 without departing from the spirit and scope of the subject matter described herein. Furthermore, the method 400 can be implemented in any suitable system hardware, software, firmware, or combination thereof. However, for ease of explanation, in the embodiments described below, the method 400 may be considered to be implemented in the above described system 100

At block 402, the on-board sensors unit 106, having plurality of sensors 106a-106d measure the pollution data in the air.

At block 404, the operations of the on-board sensor unit 106 may be controlled through a power control unit 102 connected with the on-board sensor unit 106.

At block 406, the microcontroller 110 generates the control signal to be transmitted to the power control unit 102 for controlling the operation of the on-board sensor unit 106.

At block 408, information regarding operation of the on-board sensor unit 106 at each measurement cycle of measuring the pollution data from the base station 112 may be received through the microcontroller 110.

At block 410, the air purification unit 108 receives the pollution data from the microcontroller 110.

At block 412, the microcontroller 110 enables activation or deactivation of the air purification unit 100 based on comparison of the pollution data with predefined threshold values.

Details of the method 400 are similar to details of the pollution monitoring system 100 and hence are not repeated for the sake of brevity.

Figure 5:
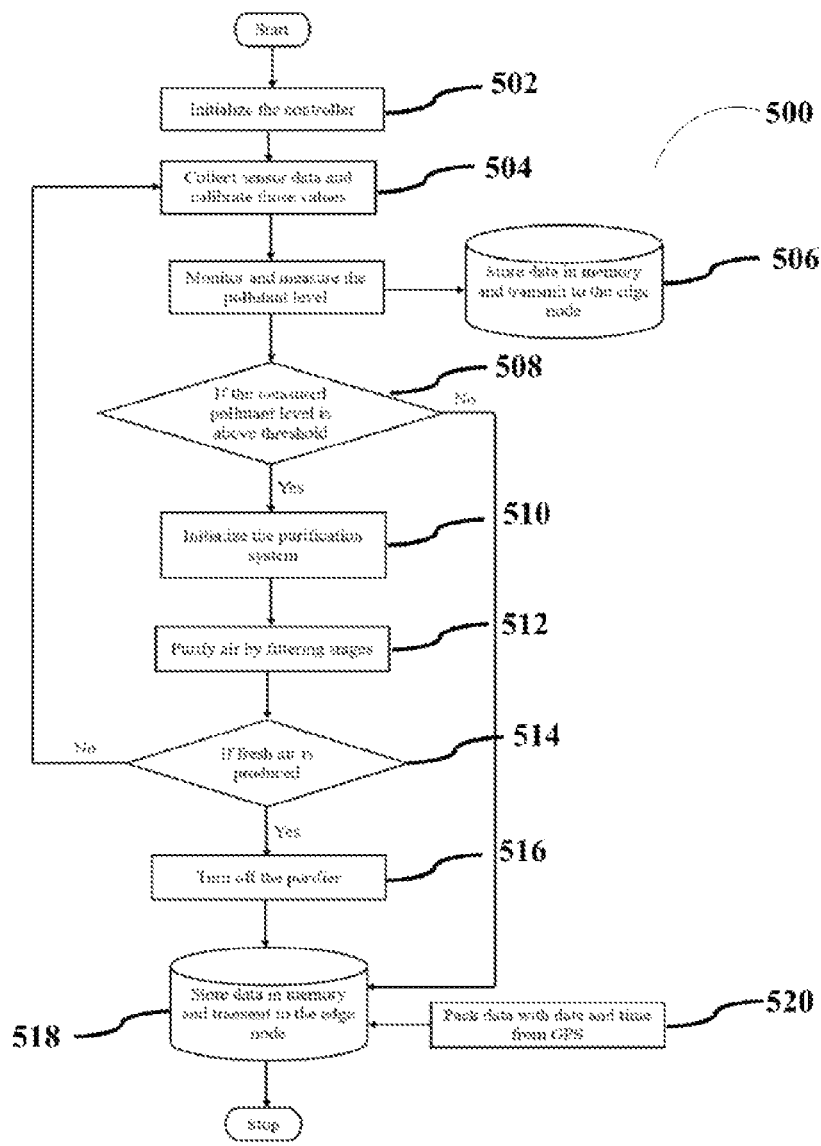
FIG. 5 illustrates flow chart for pollution monitoring system, in accordance with an embodiment of the present subject matter.

In accordance with an exemplary embodiment illustrated in FIG. 5, at step 502, in first measurement cycle of measuring the pollution data, the microcontroller 110 is initialized and collects the pollution data from the on-board sensor unit 106 (at step 504) and the microcontroller 110 calibrates the sensors 106 according to the coefficients calculated at the base station 112. Further, the on-board sensor unit 106 further monitors and measures the pollution data from the ambient environment, detects the pollution level and store/transmitted data to the edge node via NB-IoT communication channel (at step 506). If the measured pollutant level is above the threshold level, then the purification unit activates and purifies the air (steps 510, 512). At step 516, the air purification unit 108 is switched off after producing the purified air (shown in 516). If the air purification unit 108 is not producing the purified air, the pollution monitoring system 100 again starts the measurement cycle of collecting the pollution data and repeats steps 502 to step 510. Once the purified air is produced, data associated with the purified air (i.e., Air Quality Index of the purified air) is then stored in the memory (shown in step 518) and is then again transmitted back to the sensor node 106 (also referred as edge node). The data regarding the purified air is associated with a timestamp from GPS (shown in step 520).

Figure 6:
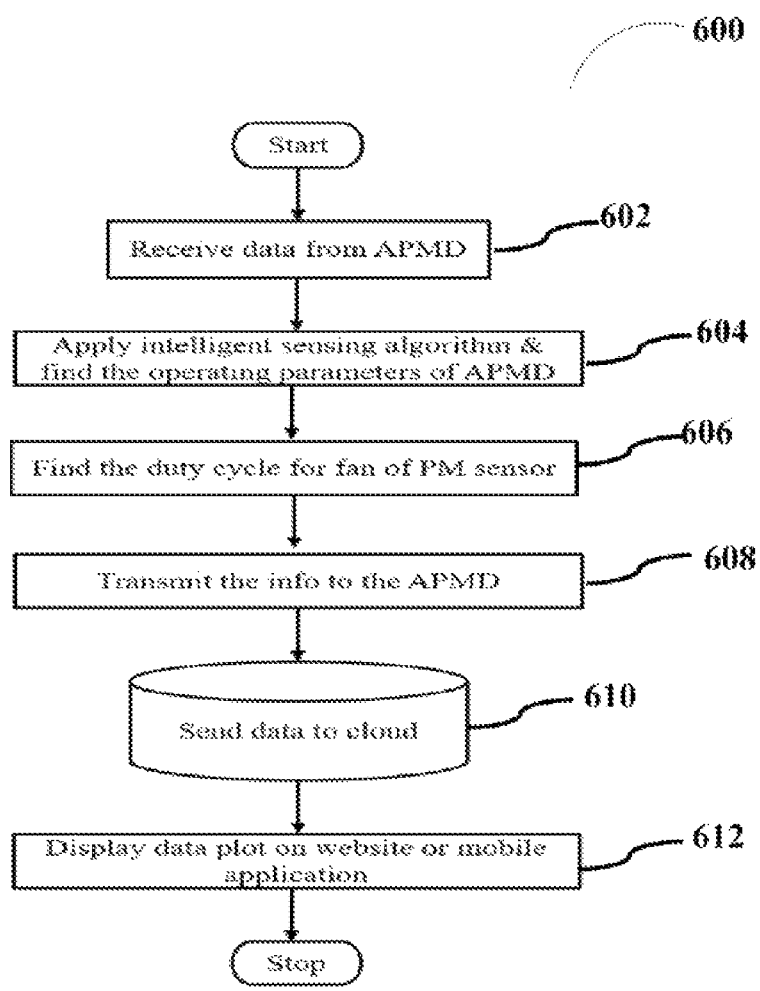
FIG. 6 illustrates flow chart for monitoring of the air pollution at the base station, in accordance with an embodiment of the present subject matter.

In an embodiment FIG. 6 illustrates the method details towards monitoring of the air pollution at the base station 112 is now discussed. At step 602, once the pollution data is received from the pollution monitoring system 100, the edge node applies learning based intelligent sensing algorithm to find optimum operating parameter like, sampling period of the sensors, optimal sensor set and length of measurement cycle for the pollution monitoring system 100 (shown in step 604). The optimum operating parameter are then shared with the microcontroller 106 for generating the control signals. As shown on step 606, to find the optimal duty cycle of the fan of PM sensor 106d optimization function is solved at the edge node based on the tradeoff between the error and the energy available at the pollution monitoring system 100. At step 608, the information regarding duty cycle is then transmitted back to the pollution monitoring system 100. After transmitting the information to the microcontroller 106, the base station 112 sends all the pollution data to a cloud server for further analysis 610. The pollution data may be accessed from a web browser or mobile application and may also be displayed on a mobile device (as shown in step 612).

In an embodiment, the disclosed pollution monitoring system 100 consumes in the range 40 mW-50 mW and may be further reduced with incorporation of edge computing aided multivariate learning framework at the sensor nodes. In contrast, the commercially available pollution monitoring systems are much higher power consuming, in the range 2 to 3 W.

Exemplary embodiments discussed above may provide certain advantages. Though not required to practice aspects of the disclosure, these advantages may include those provided by the following features.

Some embodiments of the pollution monitoring system 100 may optimize the power consumption of the PM sensor.

Some embodiments of the pollution monitoring system 100 may enable estimation of duty cycle by solving trade off the energy available at the battery of the APMD and the signal reconstruction error.

Some embodiments of the pollution monitoring system 100 may enable stronger communication over the long range.

The invention claimed is:

1. A pollution monitoring system, comprising:
   an on-board sensor unit having a plurality of sensors, configured for monitoring air quality by measuring pollution data in the air;
   a power control unit connected with the on-board sensor unit for controlling the operation of the on-board sensor unit;
   a microcontroller configured for generating control signals to be transmitted to the power control unit for controlling the operation of the on-board sensor unit, the microcontroller is configured for:
      receiving information from a base station, regarding operation of the on-board sensor unit at each measurement cycle of measuring the pollution data, wherein the information comprises a sampling interval of the on-board sensor unit and a number of sensors to be activated from the plurality of sensors in a next measurement cycle, wherein the activation of the number of sensors is identified at the base station based on the pollution data collected by the microcontroller at a previous measurement cycle; and
   an air purification unit configured for:
      receiving the pollution data from the microcontroller; and
      enabling activation or deactivation of the air purification unit based on comparison of the pollution data with predefined threshold values.

2. The pollution monitoring system as claimed in claim 1, wherein the on-board sensor unit comprises a temperature sensor, a humidity sensor, a gas sensor, and an on-board particulate matter sensor.

3. The pollution monitoring system as claimed in claim 1, wherein the control signal comprises a pulse width modulation signal applied at the switch to control activation period of a fan used in the particulate matter sensor configured in the on-board sensor unit, wherein the pulse width modulation signal is applied according to a duty cycle decided by the base station, wherein the duty cycle is decided according to availability of a rechargeable battery powering the pollution monitoring system and signal reconstruction error threshold determined by the base station;
   wherein the pulse width modulation signal activates the fan at different duty cycles when the on-board sensor unit measures the pollution data.

4. The pollution monitoring system as claimed in claim 1, wherein the microcontroller is configured for:
   auto-calibrating the pollution data by using a polynomial regressor, wherein coefficients of the polynomial regressor are computed at the base station and wherein the coefficients are updated periodically at the on-board sensing unit according to the control signals.

5. The pollution monitoring system as claimed in claim 1, comprising:
   a GPS module for tracking location of the pollution monitoring system, wherein the location is transmitted to the base station through the microcontroller, wherein the location is transmitted after the deployment of the pollution monitoring system to learn its exact geographic location;
   a memory module configured for storing the pollution data at end of each monitoring cycle; and
   a communication unit configured for establishing communication between the microcontroller and the base station, wherein the communication unit comprises a 5GeMTC protocol NB-IoT, a Wi-Fi module, or a Bluetooth.

6. The pollution monitoring system as claimed in claim 1, comprising:
   a power management unit powering the pollution monitoring system, wherein the power management unit comprises:
      a solar cell connected to the pollution monitoring system;
      a solar energy harvester for harvesting energy from the solar cell; and
      a rechargeable battery for storing the energy harvested by the solar energy harvester.

7. The pollution monitoring system as claimed in claim 1, wherein the air purification system comprises:
   an air inlet for receiving polluted air;
   a system analyzer for comparing the pollution data of the polluted air with the predefined threshold values, wherein the air purification unit is activated for producing purified air in case the pollution data is more than the predefined threshold values defined according to air quality index;
   an air purifying filter for purifying the polluted air to be supplied to an air pump by a DC fan, wherein the polluted air is further supplied to an air purifier chamber; and a purified air outlet for producing the purified air, wherein the microcontroller turns off the air purification unit after production of the purified air.

8. The pollution monitoring system as claimed in claim 1, wherein the base station is configured for:
receiving pollution data from the microcontroller at each measurement cycle, wherein the microcontroller is connected to an on-board sensing unit acting as a sensor node configured for measuring the pollution data;
determining information regarding operation of the sensor node, wherein the information is determined by using an adaptive sensing algorithm wherein the information comprises sampling interval of the on-board sensor unit and number of sensors to be activated from the plurality of sensors configured in the on-board sensing unit, in a next measurement cycle, wherein the activation of the number of sensors is identified based on pollution data collected by the microcontroller at a previous measurement cycle;
wherein the information is used by the microcontroller for generating control signals controlling operation of each of the sensors and an air purification unit connected to the microcontroller for purifying the air.

9. The pollution monitoring system as claimed in claim 1, wherein the base station is configured for:
enabling auto-calibration of the pollution data by the microcontroller by generating coefficients of a polynomial regressor to be used by the microcontroller, wherein the coefficients are updated periodically at the sensor node according to the control signals.

10. A method facilitating air pollution monitoring, the method comprising:
measuring, through an on-board sensor unit having a plurality of sensors, pollution data in the air;
controlling, through a power control unit connected with the on-board sensor unit, operation of the on-board sensor unit;
generating, through a microcontroller, control signals to be transmitted to the power control unit for controlling the operation of the on-board sensor unit;
receiving, through the microcontroller, information from a base station, regarding operation of the on-board sensor unit at each measurement cycle of measuring the pollution data, wherein the information comprises a sampling interval of the on-board sensor unit and a number of sensors to be activated from the plurality of sensors in a next measurement cycle wherein the activation of the number of sensors is identified at the base station based on the pollution data collected by the microcontroller at a previous measurement cycle and shared with the base station;
receiving, by an air purification unit, the pollution data from the microcontroller; and
enabling, by the microcontroller, activation or deactivation of the air purification unit based on comparison of the pollution data with predefined threshold values.

11. The method as claimed in claim 10, wherein the control signal comprises a pulse width modulation signal applied at the switch to control the activation period of a fan used in the particulate matter sensor configured in the on-board sensor unit, wherein the pulse width modulation signal is applied according to a duty cycle decided by the base station, wherein the duty cycle is decided according to availability of a rechargeable battery powering the pollution monitoring system and signal reconstruction error threshold determined by the base station;
wherein the pulse width modulation signal activates the fan at different duty cycles when the on-board sensor unit measures the pollution data.

12. The method as claimed in claim 10, comprising:
auto-calibrating, through the microcontroller, the pollution data by using a polynomial regressor, wherein coefficients of the polynomial regressor are computed at the base station and wherein the coefficients are updated periodically at the on-board sensing unit according to the control signals.

13. A method as claimed in claim 10, the method comprising:
receiving, at a base station, pollution data from a microcontroller at each measurement cycle, wherein the microcontroller is connected to an on-board sensing unit acting as a sensor node configured for measuring the pollution data; and
determining, at the base station, information regarding operation of the sensor node, wherein the information is determined by using an adaptive sensing algorithm, wherein the information comprises sampling interval of the on-board sensor unit and number of sensors to be activated from the plurality of sensors in a next measurement cycle, wherein the activation of the number of sensors is identified at the base station based on pollution data collected by the microcontroller at a previous measurement cycle;
wherein the information is used by the microcontroller for generating control signals controlling operation of each of the sensor node and an air purification unit connected to the microcontroller for purifying the air.

14. The method as claimed in claim 13, comprising:
enabling auto-calibration of the pollution data by the microcontroller by generating coefficients of a polynomial regressor, wherein the coefficients are updated periodically at the sensor node according to the control signals.

* * * * *